(12) United States Patent
Takahashi et al.

(10) Patent No.: US 7,791,721 B2
(45) Date of Patent: Sep. 7, 2010

(54) SURFACE INSPECTION WITH VARIABLE DIGITAL FILTERING

(75) Inventors: Kazuo Takahashi, Ninomiya (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 287 days.

(21) Appl. No.: 11/878,197

(22) Filed: Jul. 23, 2007

(65) Prior Publication Data

US 2008/0027665 A1 Jan. 31, 2008

(30) Foreign Application Priority Data

Jul. 31, 2006 (JP) .............................. 2006-207342

(51) Int. Cl.
*G01N 21/88* (2006.01)
(52) U.S. Cl. .................................. 356/237.2
(58) Field of Classification Search .... 356/237.2–237.6
See application file for complete search history.

(56) References Cited

U.S. PATENT DOCUMENTS 6,529,270 B1 * 3/2003 Bills ....................... 356/237.2

2003/0046321 A1 * 3/2003 Raymond et al. ........... 708/300

FOREIGN PATENT DOCUMENTS

JP 63-143830 6/1988

* cited by examiner

*Primary Examiner*—Gregory J Toatley, Jr.
*Assistant Examiner*—Rebecca C Slomski
(74) *Attorney, Agent, or Firm*—McDermott Will & Emery LLP

(57) ABSTRACT

A semiconductor wafer, which is an inspection object, is stuck by vacuum on a chuck and this chuck is mounted on an inspection object movement stage consisting of a rotational stage and a translational stage, located on a Z-stage. The rotational stage provides a rotational movement and the translational stage provides a translational movement. And when a foreign particle or a defect on an inspection object surface is detected, the parameter of digital filtering is dynamically changed during inspection, and the foreign particle or the defect is differentiated using the result after removing a low frequency fluctuation component to be a noise component.

18 Claims, 4 Drawing Sheets

SIDE VIEW

PLAN VIEW

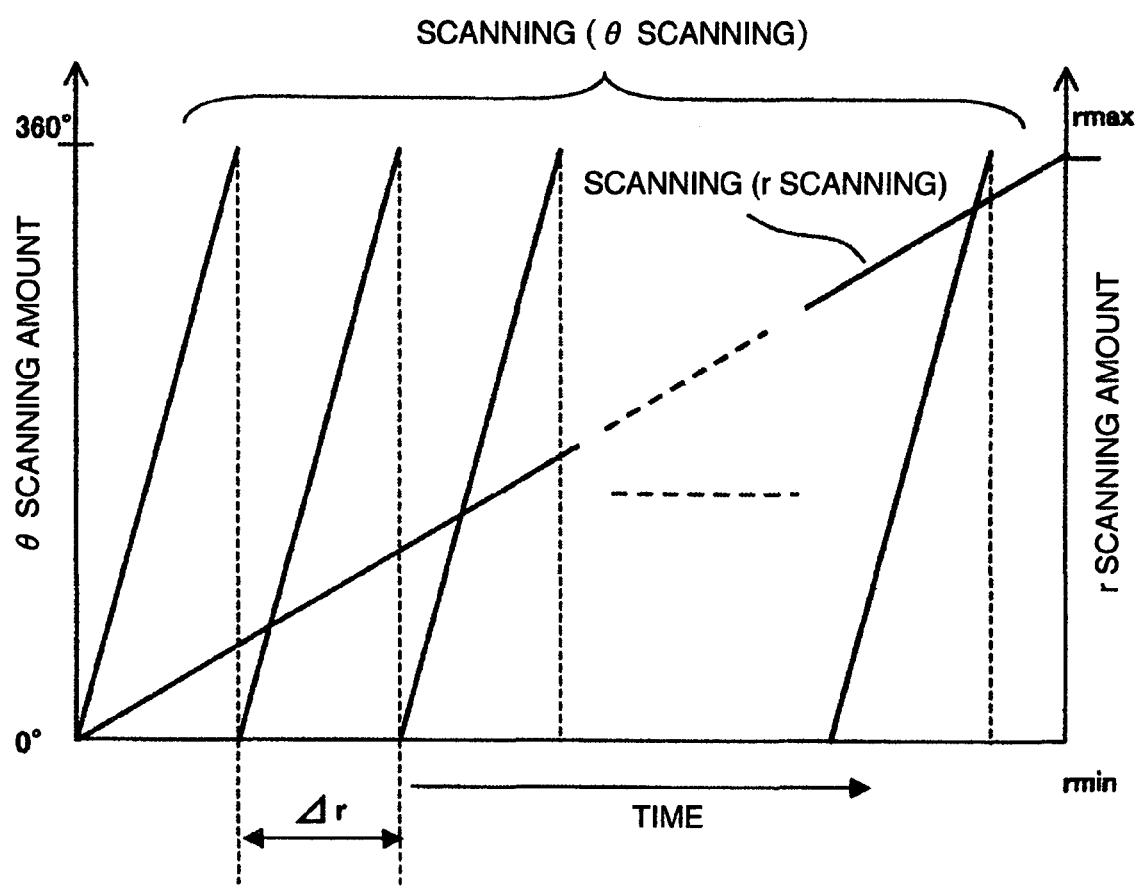

SURFACE INSPECTION WITH VARIABLE DIGITAL FILTERING

BACKGROUND OF THE INVENTION

The present invention relates to a method for inspecting a foreign particle or a defect and the like present on a surface of an inspection object, and an apparatus for inspecting the foreign particle, the defect or the like.

In a surface inspection, for example, a circuit is formed by pattern transfer on a bare-wafer and following etching, in a manufacturing process for a semiconductor device. In various manufacturing processes of a semiconductor device for forming a circuit, a foreign particle or a defect and the like attached on a bare-wafer surface accounts for a significant factor of lowering a yield. A foreign particle or a defect attached on a wafer surface is controlled in each step of manufacturing processes, and an apparatus to detect a foreign particle attached on a bare-wafer surface or a defect present on a wafer surface and the like with high sensitivity and high throughput, is a wafer surface inspection apparatus.

Methods to detect a foreign particle or a defect on a wafer surface are mainly classified into methods using a charged particle beam of an electron beam or the like and methods using a light beam, and the methods using a light beam include a method to take an image of a wafer surface by using a camera and analyze image information and a method to detect a scattered light on a wafer surface by a light receiving element like a photoelectron multiplier tube and analyze the extent of light scattering. The latter includes JP-A-63-143830.

In a surface detection apparatus of a method in which a laser beam is irradiated on a wafer, generally a laser beam is irradiated on a wafer surface and a scattered light generated from a foreign particle by the irradiation, is detected by a detector and A/D-converted, and then the size of a foreign particle/defect is calculated from digital data obtained after A/D conversion. To attain high throughput of inspection, a method is adopted that an inspection table, where a work (a wafer) is mounted, is rotated at high speed, and a stage where the inspection table is horizontally mounted in uniaxial direction, is scanned. Based on size information on a foreign particle/defect and coordinate information from the stage, a foreign particle/defect map on an entire surface of the work is calculated.

Aside from a signal generated from a foreign particle/defect of a detection object, reflected light from an inspection object includes a low frequency fluctuation component depending on surface condition, film type or film thickness, and surface roughness. In addition, influenced by vibration or the like from an inspection object movement unit, a low frequency component is generated. This low frequency component is not constant, because it is decided by parameters consisting of a size of illumination light, a speed of the inspection object movement unit and movement position.

Conventionally, though the frequency component was removed or controlled by an analogue filter, since it is difficult for a Cut-off frequency setting to be flexibly varied as being determined by a circuit constant, it was difficult to respond to each of the conditions described above.

In addition, considering distortion of a passing signal, since a passing signal band is required to have a margin, it was hard to have an attenuation frequency band sufficiently wide, and it was difficult for the low frequency component to be removed or controlled accurately.

Accordingly, since a detection determination threshold level has to be raised by the degree of the low frequency fluctuation component remaining after passing the analogue filter, there remained a problem that detection sensitivity was deteriorated by this degree.

In addition, depending on surface condition, film type or film thickness, and surface roughness, reflected light generated from a foreign particle/defect varies itself, therefore there was a problem that it was difficult to respond only with a fixed threshold.

SUMMARY OF THE INVENTION

An object of the present invention is to provide a surface inspection apparatus and a surface inspection method enabling to respond to a wide variety of wafers with a different kind of film type, film thickness, surface roughness and crystal orientation or the like.

In addition, another object of the present invention is to provide a surface inspection apparatus and a surface inspection method enabling to reduce the influence received from an inspection object movement unit of the inspection apparatus itself, and enhance the accuracy of detection determination.

According to one embodiment of the present invention, in digital filtering of a signal obtained by a surface inspection, at least one parameter for the digital filtering is dynamically varied during inspection.

According to another embodiment of the present invention, in digital filtering of a signal obtained by a surface inspection, at least one parameter for the digital filtering is controlled in response to a radius of an inspection object.

According to still another embodiment of the present invention, a surface inspection apparatus for detecting a foreign particle or a defect present on an inspection object surface or inside the proximity of the surface is configured so as to detect a foreign particle/defect by using results obtained by a removing treatment of an undesired low frequency fluctuation component.

It is desirable that the removing treatment of the undesired low frequency fluctuation component be accomplished by a digital filtering treatment of plurality of digital data obtained from a signal received at the surface inspection.

It is desirable that the digital filtering treatment be a frequency band limitation filtering treatment which removes the undesired low frequency fluctuation component.

It is desirable that the frequency band limitation filtering treatment be a low-pass filtering treatment which extracts the undesired low frequency fluctuation component and be configured so as to subtract the result of the low-pass filtering treatment from the digital data.

It is desirable that the frequency band limitation filtering treatment be a high-pass filtering treatment or a band-pass filtering treatment which removes the undesired low frequency fluctuation component.

In addition, it is desirable that the Cut-off frequency of the digital filtering treatment be variable.

In addition, it is desirable that the Cut-off frequency of the frequency band limitation filtering treatment be determined based on any one or a combination of plurality of (1) a main scanning rotational speed of an inspection object movement stage, (2) coordinate position in the sub-scanning direction obtained by the above coordinate detection unit (3) a size of an illumination spot, and be set every time when a condition varies.

In addition, when the above particle diameter calculation device determines the Cut-off frequency of the frequency band limitation filtering treatment, it is desirable to use further any one or a combination of plurality of (1) type or thickness of film formed (2) surface roughness (3) crystal orientation (4) warpage amount, on an inspection object surface.

According to the present invention, even in the case of different surface conditions of an inspection object, as it is possible to reduce the low frequency component of the reflected light, it is not necessary to raise a detection determination threshold level, therefore a weak signal can be detected and an inspection object can be accurately measured.

Alternatively, because reduction of the low frequency component of the reflected light is enabled in each condition of a size of illumination light, a speed of an inspection object movement unit or movement position, a proper threshold can be set.

Alternatively, even in the case that surface condition of an inspection object differs depending on film type or film thickness, surface roughness, inspection can be executed with the same performance as in the case of a standard wafer.

Alternatively, because of no signal distortion caused by analogue filtering, a passing signal has no distortion and it is possible to narrow passing band width and further to obtain symmetric attenuation property in both bands, therefore, an accurate inspection can be accomplished.

Other objects, features and advantages of the invention will become apparent from the following description of the embodiments of the invention taken in conjunction with the accompanying drawings.

BRIEF DESCRIPTION OF THE DRAWINGS

FIG. 3 shows scanning according to one embodiment of the present invention.

DESCRIPTION OF THE INVENTION

Although the following description will be made below on embodiments of the present invention using the accompanying drawings, the apparatus and the method according to the present invention are not limited to the configurations shown in each drawing and various changes and modifications may be made within the spirit of the invention.

Figure 1:
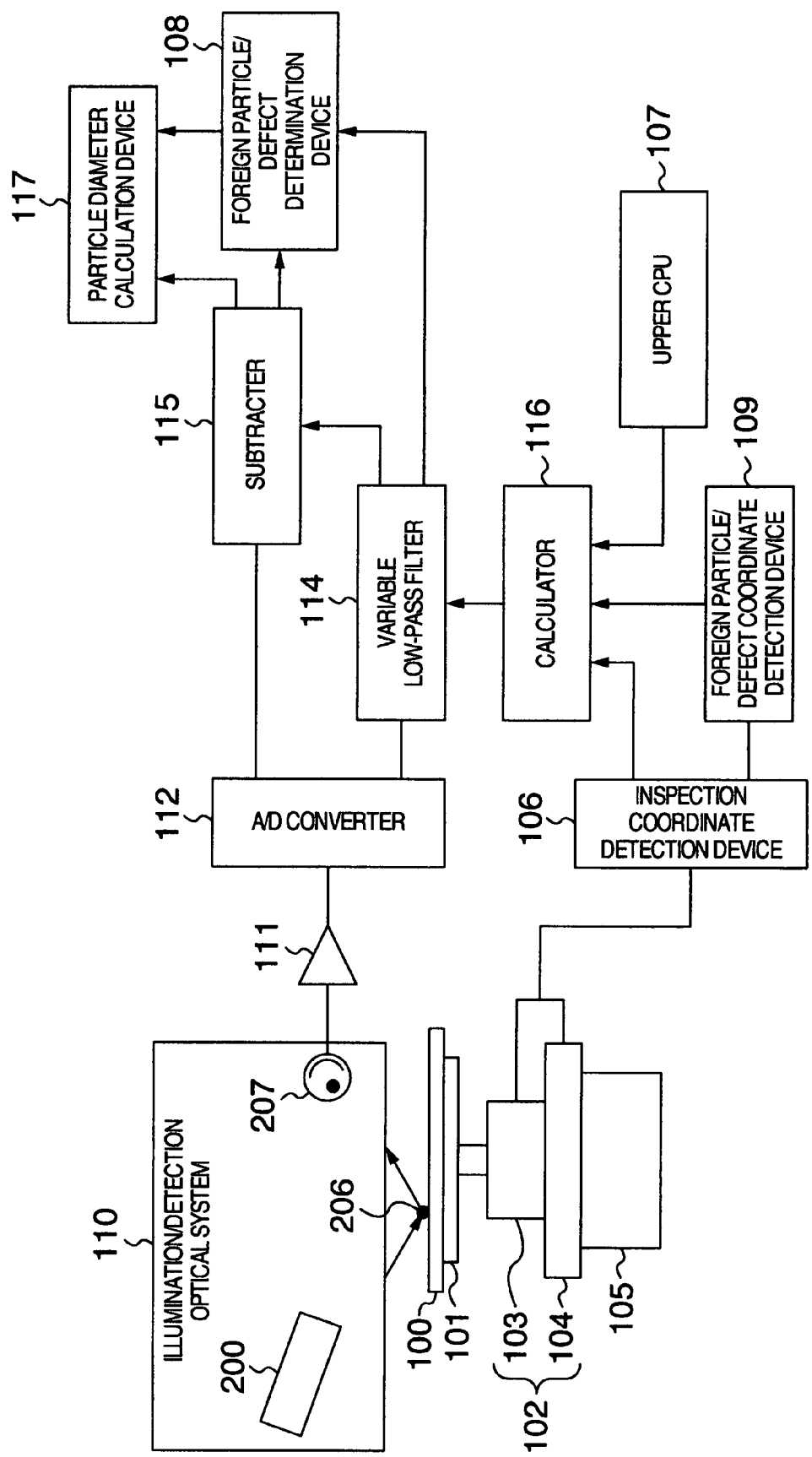
FIG. 1 shows a schematic configuration according to one embodiment of the present invention.

FIG. 1 shows first embodiment of a foreign particle/defect inspection apparatus using a foreign particle/defect detection method according to the present invention. The semiconductor wafer 100, which is an inspection object, is stuck fast to the chuck 101 by vacuum and this chuck 101 is mounted on the Z-stage 105 via the inspection object movement stage 102 configured with a rotational movement unit, which is capable of scanning with a nearly constant rotational angle speed, consisting of the rotational stage 103, and a translational movement unit consisting of the translational stage 104. The rotational movement θ is carried out on the rotational stage 103 and the translational movement r is carried out on the translational stage 104.

Figure 2A:
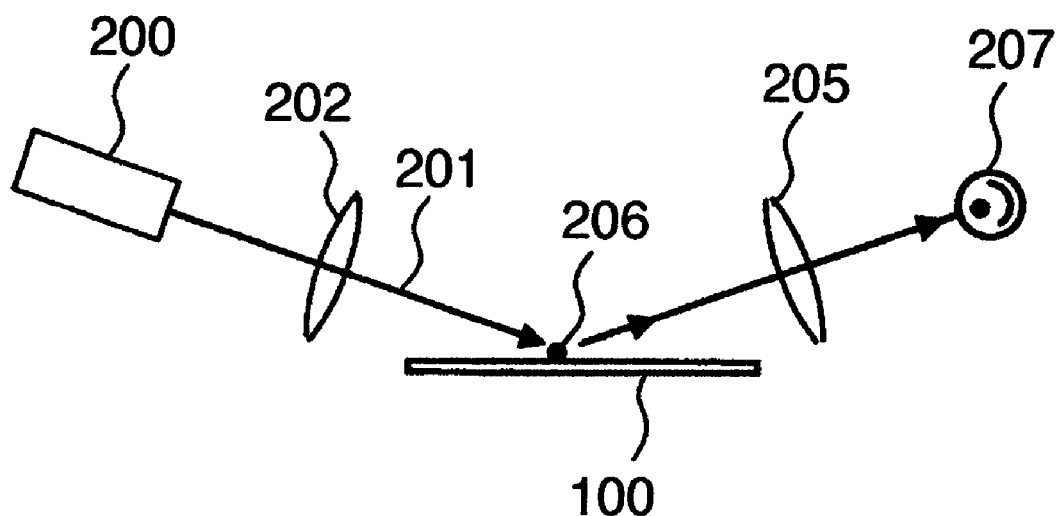
FIG. 2A shows a side view of an illumination spot according to one embodiment of the present invention.
Figure 2B:
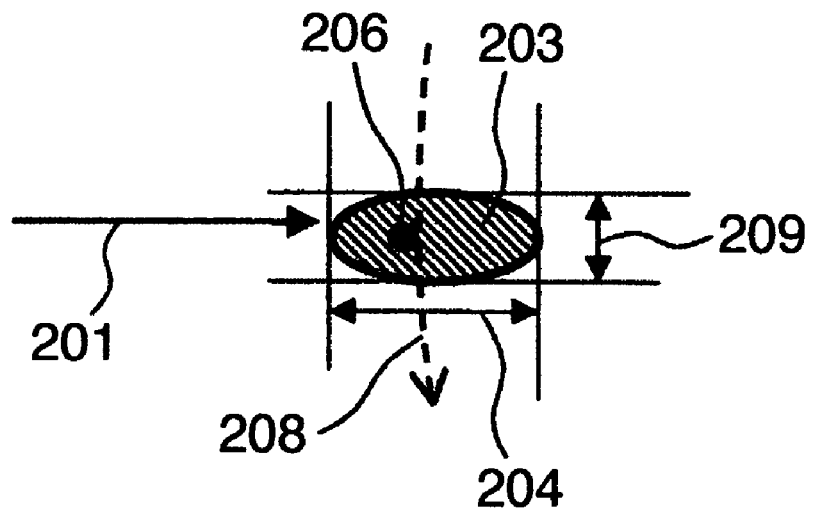
FIG. 2B shows a plan view of an illumination spot according to one embodiment of the present invention.

FIGS. 2A and 2B are a plan view and a side view showing the illumination/detection optical system 110 located above the semiconductor wafer 100. An illumination unit according to the present embodiment uses a laser light source as the light source 200 of an illumination light. The irradiating light 201 consisting of a laser light shot from the light source 200 enters into the irradiating lens 202 and the illumination spot 203 with a predetermined size is formed. The irradiating light 201 is, for example, P polarization, and is configured so as to enter obliquely with approximately Brewster's angle to crystal Si, on a surface of the semiconductor wafer 100, which is an inspection object. Therefore, the illumination spot 203 is substantially oval-shaped, and the inside area of a contour line where illuminance comes down to $1/e^2$ (e: base of natural logarithm) of that at the center of the illumination spot 203, is defined anew as the illumination spot.

The width 204 in the long axis direction of the illumination spot 203 is described as d1 and the width 209 in the short axis direction of the same is described as d2. With the illumination spot 203, θ-scanning 208 is executed as indicated by the dotted arrow in FIG. 2B.

As shown in FIG. 3, by changing and combining with time the rotational movement θ and the translational movement r, the inspection object movement stage 102 causes relatively the illumination spot 203 to scan spirally on the approximately whole surface of the semiconductor wafer 100. While the rotation stage rotates one turn, scanning moves as much as the distance Δr. When Δr>d1, because an illumination light is not radiated on the semiconductor wafer 100 in spiral scanning and gap area not to be inspected is formed, normally a setting of Δr<d1 is used. Although, in the present embodiment, scanning of the illumination spot 203 is executed from the inner periphery toward the outer periphery of the semiconductor wafer 100, the reverse scanning direction is acceptable.

Figure 4:
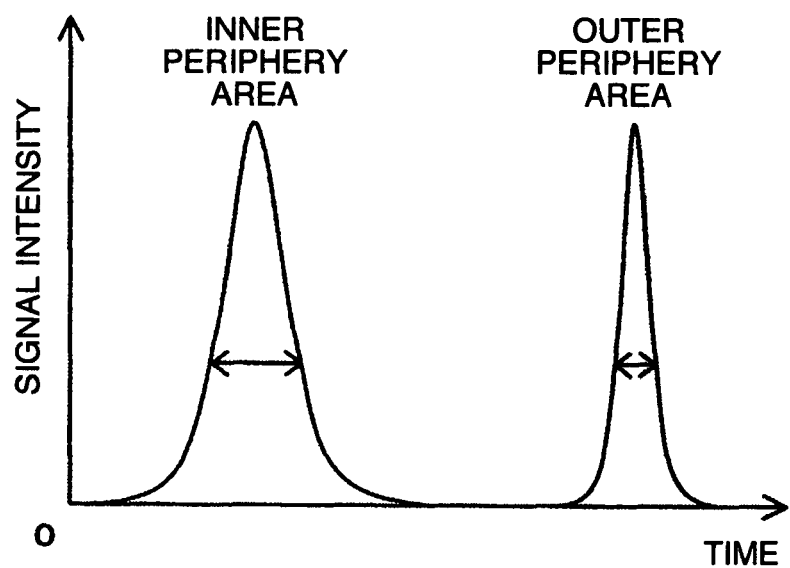
FIG. 4 shows the difference (the signal width difference) of a foreign particle/defect signal caused by the scanning position difference according to one embodiment of the present invention

In addition, in the embodiment, in the approximately whole area from the inner periphery toward the outer periphery of the semiconductor wafer 100, the rotational stage 103 is driven at a approximately constant angular speed and the translational stage 104 is driven nearly at a constant linear speed. FIG. 4 shows, as a result of the above, the relative movement linear speed of the illumination spot 203 to the surface of the semiconductor wafer 100, becomes larger at the outer periphery area compared with that at the inner periphery area.

On the inspection object movement stage 102, the inspection coordinate detection device 106 is provided in order to detect the main-scanning coordinate position θ and the sub-scanning coordinate position r. Although, in the present embodiment, as a means of obtaining position information, a rotary encoder (primary position acquisition section) of an optical scanning type is used to detect the main-scanning coordinate position θ, and a linear encoder (secondary position acquisition section) of an optical scanning type is used to detect the sub-scanning coordinate position r, instead of both encoders, other type detectors with a different detection principle may be used as long as a sensor capable of detecting an angle or a position on a straight line with high accuracy is used.

The collecting lens 205 is configured so as to collect a scattered light with a low elevation angle in order to collect efficiently the scattered light even from a minute foreign particle which follows Rayleigh scattering. In this configuration, the scattered light from the foreign particle/defect 206 passes the collecting lens 205 and is detected by a light detection unit consisting of the light detector 207. The light detector 207, which detected the scattered light, converts the scattered light to an electric signal (an inspection signal) and outputs as a scattered light signal. Although, in the present embodiment, a photoelectron multiplier tube is used as the light detector 207, other light detectors with different detection principles may be used as long as the light detector can detect a scattered light from a foreign particle with high sensitivity.

As described above, in the present embodiment, in the approximately whole area from the inner periphery toward the outer periphery of the semiconductor wafer 100, the rotational stage 103 is driven at an approximately constant angular speed, and the relative movement linear speed of the illumination spot 203 to the surface of the semiconductor wafer 100 becomes bigger at the outer periphery compared with that at the inner periphery. Therefore, a time period while a foreign particle on the semiconductor wafer 100 crosses the short axis 209 and the width d2 of the illumination spot 203, is smaller in the case where the foreign particle is present in an outer periphery area of the semiconductor wafer 100 compared with that in the case where present in an inner periphery area. Therefore, as shown in FIG. 4, time-varying wave form of a signal intensity of the scattered light signal obtained by the light detector 207 via the amplifier 111 has generally the smaller half bandwidth of signal peak, in the outer periphery area, that is, in the case where the foreign particle is present in the larger radius area of the scanning direction.

Then, a signal treatment according to the present embodiment will be explained below. After the scattered light signal, which is converted to an electric signal (an inspection signal) by the light detector 207, is amplified by the amplifier 111, the scattered light signal is sampled every sampling time interval ΔT predetermined by A/D conversion unit consisting of A/D converter 112, and converted to digital data. The sampling time interval ΔT is determined so as to be able to sample the signal wave form shown in FIG. 4 with sufficient time resolution. For example, when the half bandwidth in the most outer periphery area having the minimum signal wave form width as shown in FIG. 4, is described as ΔSout, ΔT is determined as ΔT=ΔSout/10. By this sampling, a group of time series digital data corresponding to the signal wave form shown in FIG. 4. are obtained.

Figure 5:
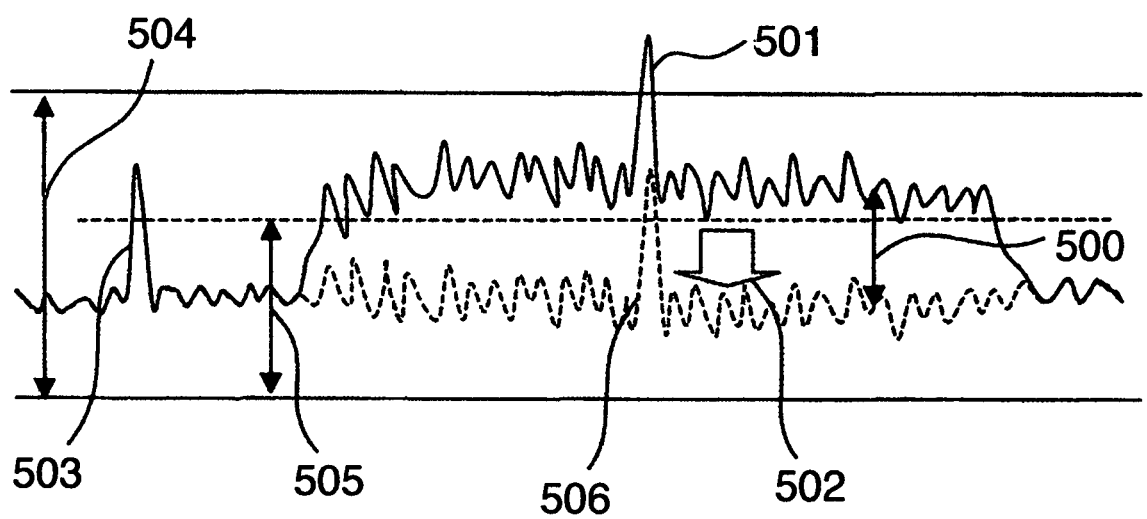
FIG. 5 shows a foreign particle/defect signal and a threshold according to one embodiment of the present invention.

Incidentally, the group of time series digital data includes the signal component 500 of low frequency as shown in FIG. 5 in addition to intensity information of the scattered light corresponding to a size of the detected foreign particle/defect, which is essentially needed. Generally, the signal component of low frequency does not become a fixed value because it varies depending on a main scanning rotational speed of the inspection object movement stage, coordinate information in the scanning direction obtained by the coordinate detection unit, the size of the illumination spot, and further, type or thickness of film formed, surface roughness, crystal orientation and warpage amount on the inspection object surface. Therefore, in order to calculate correctly a size of the foreign particle/defect, it is necessary to remove the influence from the low frequency component.

Consequently in the present embodiment, toward the digital data from the A/D converter 112, the data of only the low frequency component is generated by the variable low-pass filter 114 treatment as one example of digital filtering, followed by subtraction by the subtracter 115 from data obtained by the A/D converter 112 (digital filtering section) and only the intensity information of the scattered light corresponding to the size of the foreign particle/defect is extracted.

Here, the Cut-off frequency which is one example of a parameter of the variable low-pass filter 114, is dynamically controlled by the calculator 116 (parameter changing section), based on the information including rotational speed of an inspection object movement stage, coordinate position in the scanning direction obtained by the coordinate detection unit, size of the illumination spot, further, type or thickness of film formed, surface roughness, crystal orientation and warpage amount on the inspection object surface. The calculation parameter of this calculator is based on information from the inspection coordinate detection device 106 and the upper CPU 107.

Cut-off frequency=1/(short radius of illumination spot/rotational speed/(2*circle ratio*radius coordinate position))/A "A" is specified from film type, film thickness, surface roughness, crystal orientation and warpage amount.

Film type, film thickness, surface roughness, crystal orientation and warpage amount are set by a user via an input unit not shown, and calculated in an inspection apparatus. As this input unit, a pointing device such as a keyboard or a mouse may be used. In addition, an independent memory in which necessary information described above is stored, may be input into the inspection apparatus via an interface not shown.

The scattered light intensity value obtained as a result of the data processing, is compared with the predetermined detection threshold in the foreign particle/defect determination device 108, and the foreign particle/defect determination device 108 generates foreign particle/defect determination information if the scattered light intensity value is not less than the threshold. When the foreign particle/defect determination information is generated, the foreign particle/defect coordinate detection device 109 calculates the coordinate position of the detected foreign particle/defect based on information from the inspection coordinate detection device 106. In addition, the particle diameter calculation device 117 calculates the size of the foreign particle/defect detected from the scattered light intensity value.

In this manner, in the present embodiment, toward the signal obtained by the amplifier 111, after removing the influence of the low frequency component by the variable low-pass filtering treatment, the size of the foreign particle/defect is calculated. By execution of parameter changing treatment where parameter of this digital filtering is varied dynamically during inspection, as shown in FIG. 5, even in the case of superposition 501 of the foreign particle/defect signal on the low frequency component, the low frequency component removal 502 causes the foreign particle/defect signal to be the detection signal 506 after the present embodiment, and since the offset by the extent of the signal component 500 of the low frequency wave is not necessary like the conventional threshold 504 and can be used as the threshold 505 after the present embodiment, the foreign particle/defect signal 503 which has not been detected conventionally, can be properly detected.

Although, in the present embodiment, after the undesired low frequency fluctuation component is extracted by the low-pass filtering treatment, the subtraction thereof from the original data provides the removal of the low frequency fluctuation component, the configuration is obviously accepted where a high-pass filtering treatment or a band pass filtering treatment in which the low frequency fluctuation component is removed directly.

The result of the surface inspection is output from an output unit not shown. As the output unit, a printing unit such as a display unit or a printer and the like, may be used. In addition, result information may be stored in a memory built in the inspection apparatus via an interface not shown. Alternatively, the result information may be stored in an independent memory via an interface not shown.

It should be noted that, according to the present embodiment, although foreign particles/defects on the inspection surface are differentiated by the electric signal (inspection signal) based on the scattered light, it is not limited to this method, furthermore, by providing a light detecting unit where a diffracted light or a reflected light, which is emitted by the irradiating light from the inspection object, is detected and converted to an electric signal (inspection signal), differentiation of foreign particles/defects can be accomplished by the electric signal (inspection signal).

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A surface inspection apparatus for detecting a foreign particle or a defect present on an inspection object surface or inside the proximity of the surface, comprising:
    an inspection object movement stage having a rotational movement unit and a translational movement unit configured so as to be able to scan said inspection object at an approximately constant rotational angular speed;
    a laser beam source;
    an illumination unit irradiating a laser beam emitted from said laser beam source on an illumination spot of a predetermined size on the inspection object surface;
    a light detection unit, which detects a light generated from said illumination spot and converts the light to an electric signal;
    an A/D converter for conversion of said electric signal into digital data;
    a particle diameter calculation device for calculating a size of the foreign particle or the defect from the digital data obtained by said A/D conversion; wherein:
    said A/D converter executes sampling of said electric signal at approximately constant sampling time intervals,
    said particle diameter calculation device executes detection of the foreign particle/defect by using a result of a removal treatment of an undesired low frequency fluctuation component on the digital data obtained by said A/D converter, and
    said particle diameter calculation device determines a parameter of the removal treatment of the undesired low frequency fluctuation component based on any plural combination of (1) type or thickness of film formed on the inspection object surface, (2) surface roughness on the inspection object surface, (3) crystal orientation on the inspection object surface, and (4) warpage amount on the inspection object surface.

2. The surface inspection apparatus according to claim 1, wherein said removal treatment of the undesired low frequency fluctuation component is a digital filtering treatment of plural digital data sampled from said electric signal within a transit time in said illumination spot.

3. The surface inspection apparatus according to claim 2, wherein said digital filtering treatment is a frequency band limitation filtering treatment which removes said undesired low frequency fluctuation component.

4. The surface inspection apparatus according to claim 3, wherein said frequency band limitation filtering treatment is a low-pass filtering treatment which extracts said undesired low frequency fluctuation component and is configured so as to subtract the result of said low-pass filtering treatment from the digital data obtained by said A/D conversion.

5. The surface inspection apparatus according to claim 3, wherein said frequency band limitation filtering treatment is a high-pass filtering treatment or a band-pass filtering treatment which removes said undesired low frequency fluctuation component.

6. The surface inspection apparatus according to claim 3, wherein the Cut-off frequency of said digital filtering treatment is variable.

7. The surface inspection apparatus according to claim 6, wherein said particle diameter calculation device determines the Cut-off frequency of said frequency band limitation filtering treatment based on any one or plural combination of (1) a main scanning rotational speed of the inspection object movement stage, (2) a coordinate position in the sub-scanning direction obtained by said coordinate detection unit (3) a size of the illumination spot, and is configured so as to be set as needed when said information varies.

8. The surface inspection apparatus according to claim 7, wherein, when said particle diameter calculation device determines the Cut-off frequency of said frequency band limitation filtering treatment, said particle diameter calculation device is configured to use (1) the type or thickness of film formed, (2) the surface roughness, (3) crystal orientation and (4) the warpage amount.

9. A surface inspection apparatus for detecting a foreign particle or a defect present on said inspection object surface or inside the proximity of the surface, while scanning an inspection object at an approximately constant rotational angular speed, comprising:
    an inspection object movement stage wherein scanning is performed by a rotational movement and a translational movement;
    a laser beam source;
    an illumination unit irradiating a laser beam emitted from said laser beam source on an illumination spot of a predetermined size on the inspection object surface;
    a light detection unit, which detects a light generated from said illumination spot and converts the light to an electric signal;
    an A/D converter for conversion of said electric signal into digital data;
    a particle diameter calculation device for calculating a size of the foreign particle or the defect from the digital data obtained by said A/D conversion; wherein:
    said A/D converter executes sampling of said electric signal at approximately constant sampling time intervals,
    said particle diameter calculation unit executes detection of a foreign particle/defect by using the result of a frequency band limitation filtering treatment removing undesired low frequency fluctuation component on the digital data obtained by said A/D conversion unit,
    a Cut-off frequency of said frequency band limitation filtering treatment is variable, and
    said particle diameter calculation device determines the Cut-off frequency of the band limitation filtering treatment based on any plural combination of (1) type or thickness of film formed on the inspection object surface, (2) surface roughness on the inspection object surface, (3) crystal orientation on the inspection object surface, and (4) warpage amount on the inspection object surface.

10. The surface inspection apparatus according to said claim 9, wherein said frequency band limitation filtering treatment is a low-pass filtering treatment which extracts said undesired low frequency fluctuation component and is configured so as to subtract the result of said low-pass filtering treatment from the digital data obtained by said A/D conversion unit.

11. The surface inspection apparatus according to claim 9, wherein said frequency band limitation filtering treatment is a high-pass filtering treatment or a band-pass filtering treatment which removes said undesired low frequency fluctuation component.

12. The surface inspection apparatus according to claim 9, wherein the plural combination on which the Cut-off frequency of said frequency band limitation filtering treatment is determined further comprises any one or more of (5) a main scanning rotational speed of the inspection object movement stage, (6) a coordinate position in the sub-scanning direction obtained by said coordinate detection unit and (7) a size of the illumination spot.

13. A surface inspection apparatus for performing a surface inspection based on an inspection signal obtained from an inspection object, comprising:
    a digital filtering section for executing digital filtering of the inspection signal obtained, and
    a parameter changing section for changing dynamically a parameter of said digital filtering during inspection, based on any plural combination of (1) type or thickness of film formed on the inspection object surface, (2) surface roughness on the inspection object surface, (3) crystal orientation on the inspection object surface, and (4) warpage amount on the inspection object surface.

14. A surface inspection apparatus for performing a surface inspection based on an inspection signal obtained from an inspection object, comprising:
    a digital filtering section for executing digital filtering of the inspection signal obtained,
    a position information acquisition section for obtaining position information of the inspection object from which said inspection signal is obtained, and
    a parameter changing section for changing a parameter of said digital filtering based on the information from the position information acquisition section and based on any plural combination of (1) type or thickness of film formed on the inspection object surface, (2) surface roughness on the inspection object surface, (3) crystal orientation on the inspection object surface, and (4) warpage amount on the inspection object surface.

15. The surface inspection apparatus according to claim 14, wherein said position information comprises at least a radius position information in response to the inspection signal obtained.

16. A surface inspection method for performing a surface inspection based on an inspection signal obtained from an inspection object, comprising:
    a digital filtering treatment for executing digital filtering of the inspection signal obtained, and
    a parameter changing treatment for dynamically changing a parameter of the digital filtering during inspection, based on any plural combination of (1) type or thickness of film formed on the inspection object surface, (2) surface roughness on the inspection object surface, (3) crystal orientation on the inspection object surface, and (4) warpage amount on the inspection object surface.

17. A surface inspection method for performing a surface inspection based on an inspection signal obtained from an inspection object, comprising:
    a digital filtering treatment for executing digital filtering of the inspection signal obtained,
    a position information acquisition treatment for obtaining the position information of the inspection object, which said inspection signal was obtained, and
    a parameter changing treatment for changing parameter of said digital filtering based on information from the position information acquisition treatment and based on any plural combination of (1) type or thickness of film formed on the inspection object surface, (2) surface roughness on the inspection object surface, (3) crystal orientation on the inspection object surface, and (4) warpage amount on the inspection object surface.

18. The surface inspection method according to claim 17, wherein said position information comprises at least a radius position information of the inspection object corresponding to the inspection signal obtained.

* * * * *